US00PP31369P2

(12) United States Plant Patent
Probst

(10) Patent No.: US PP31,369 P2
(45) Date of Patent: Jan. 14, 2020

(54) ***COREOPSIS* PLANT NAMED 'GLOWING EMBERS'**

(50) Latin Name: ***Coreopsis* hybrid**
Varietal Denomination: Glowing Embers

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 15/998,102

(22) Filed: Jun. 29, 2018

(51) Int. Cl.
*A01H 5/02* (2018.01)
*A01H 6/14* (2018.01)

(52) U.S. Cl.
USPC ..... Plt./417

(58) Field of Classification Search
USPC ..... Plt./417
CPC ... A01H 5/02; A01H 5/00; A01H 6/14; A01H 5/025
See application file for complete search history.

(56) References Cited

PUBLICATIONS

Germania Seed Company. Emerald Coast—Ornamental Grasses and Perennials 2018 Program # 22, retrieved on May 1, 2019, retrieved from the Internet at https://www.germaniaseed.com/pdf/2018/722_ecgrowers.pdf, pp. 1-12. (Year: 2018).*
Pioneer Gardens, Inc. 2017-2018 Program and Availability, retrieved on May 1, 2019, retrieved from the Internet at https://nebula.wsimg.com/2d7b6f031987cdb671ed0db49bf7efb8?AccessKeyId=D4DC3ED90C9EAD58C2B4&disposition=0&alloworigin=1, pp. 1-16 (Year: 2017).*

* cited by examiner

*Primary Examiner* — June Hwu
(74) *Attorney, Agent, or Firm* — Penny J. Aguirre

(57) ABSTRACT

A new cultivar of hybrid *Coreopsis* named 'Glowing Embers' that is characterized by its sturdy, well-branched plant habit reaching an average of 45 cm in height and 75 cm in width, its floriferous and long blooming season of sterile inflorescences that do not require deadheading; bloom commences in early July and lasts until frost in Kensington, Conn., its medium sized inflorescences with ray florets that are orange-red in color with yellow colored markings near the tips, its resistance to powdery mildew (*Podosphaera macularis*) and leafspot (*Pseudomonas cichorii*) and its cold hardiness at least to U.S.D.A. Zone 5a.

2 Drawing Sheets

Botanical classification: *Coreopsis* hybrid.
Variety denomination: 'Glowing Embers'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Publications include but are not limited to listings on ecgrowers, Santa Rosa Gardens, and Skagit Gardens.

BACKGROUND OF THE INVENTION

The present invention relates to a new and distinct cultivar of *Coreopsis* plant, botanically of hybrid origin and known as *Coreopsis* 'Glowing Embers' and will be referred to hereinafter by its cultivar name, 'Glowing Embers'. The new cultivar of *Coreopsis* is an herbaceous perennial grown for landscape and container use.

The new Invention arose from an ongoing controlled breeding program in New Braintree, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A. Zone 5 in a wide range of flower colors and plant forms that do not require vernalization to intiate flowering.

The Inventor made a controlled cross in August of 2013 in New Braintree, Mass. between an unnamed and unpatented proprietary plant from his breeding program as the female parent and pollen that was pooled from a variety of unnamed and unpatented proprietary plants from his breeding program as the male parent. The exact characteristics of the pollen parent are therefore unknown. 'Glowing Embers' was selected in September of 2014 as a single unique plant amongst the resulting seedlings.

Asexual propagation of the new cultivar was first accomplished by stem cuttings under the direction of the Inventor in Kensington, Conn. in September of 2014. Asexual propagation by stem cuttings has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Glowing Embers' as a unique cultivar of *Coreopsis*.

1. 'Glowing Embers' exhibits a sturdy, well-branched plant habit reaching an average of 45 cm in height and 75 cm in width.
2. 'Glowing Embers' exhibits a floriferous and long blooming season of nearly sterile inflorescences that do not require deadheading; bloom commences in early July and lasts until frost in Kensington, Conn.
3. 'Glowing Embers' exhibits medium sized inflorescences with ray florets that are orange-red in color with yellow colored markings near the tips.
4. 'Glowing Embers' exhibits resistance to powdery mildew (*Podosphaera macularis*) and leafspot (*Pseudomonas cichorii*).
5. 'Glowing Embers' exhibits cold hardiness at least to U.S.D.A. Zone 5a.

The female parent of 'Glowing Embers' differs from 'Glowing Embers' in having inflorescences with ray florets that are solid dark pink in color, in not being reliably hardy in U.S.D.A. Zone 5 and in having a taller plant height and more upright plant habit. 'Glowing Embers' can be most closely compared to *Coreopsis* cultivars 'Sunset Strip' (U.S. Plant Pat. No. 22,670) and 'Desert Coral' (U.S. Plant Pat. No. 24,847). 'Sunset Strip' is similar to 'Glowing Embers' in having inflorescences with ray florets that are orange in color, thread-leaf type foliage and a similar cold hardiness. 'Sunset Strip' differs from 'Glowing Embers' in having inflorescences with ray florets that in the summer months are primarily golden yellow in color with dark orange centers, in being very fertile and produces an abundance of seed, and in being more prone to powdery mildew when grown under similar conditions in New Braintree, Mass. 'Desert Coral' is similar to 'Glowing Embers' in having inflorescences with ray florets that are orange in color and in having thread-like foliage. 'Desert Coral' differs from 'Glowing Embers' in having inflorescences with ray florets that are pink-orange with a red color eye zone, in being prone to powdery mildew when grown under similar conditions in New Braintree, Mass. and in not being cold hardy in U.S.D.A. Zone 5.

BRIEF DESCRIPTION OF THE DRAWINGS

The accompanying colored photographs illustrate the overall appearance and distinct characteristics of the new *Coreopsis*. The photographs were taken of a 3-month-old plant of 'Glowing Embers' as grown outdoors in a one-gallon container from a 30-cell plug in Kensington, Conn.

The photograph in FIG. 1 provides a side view of 'Glowing Embers' and shows the plant habit in bloom.

Figure 1:
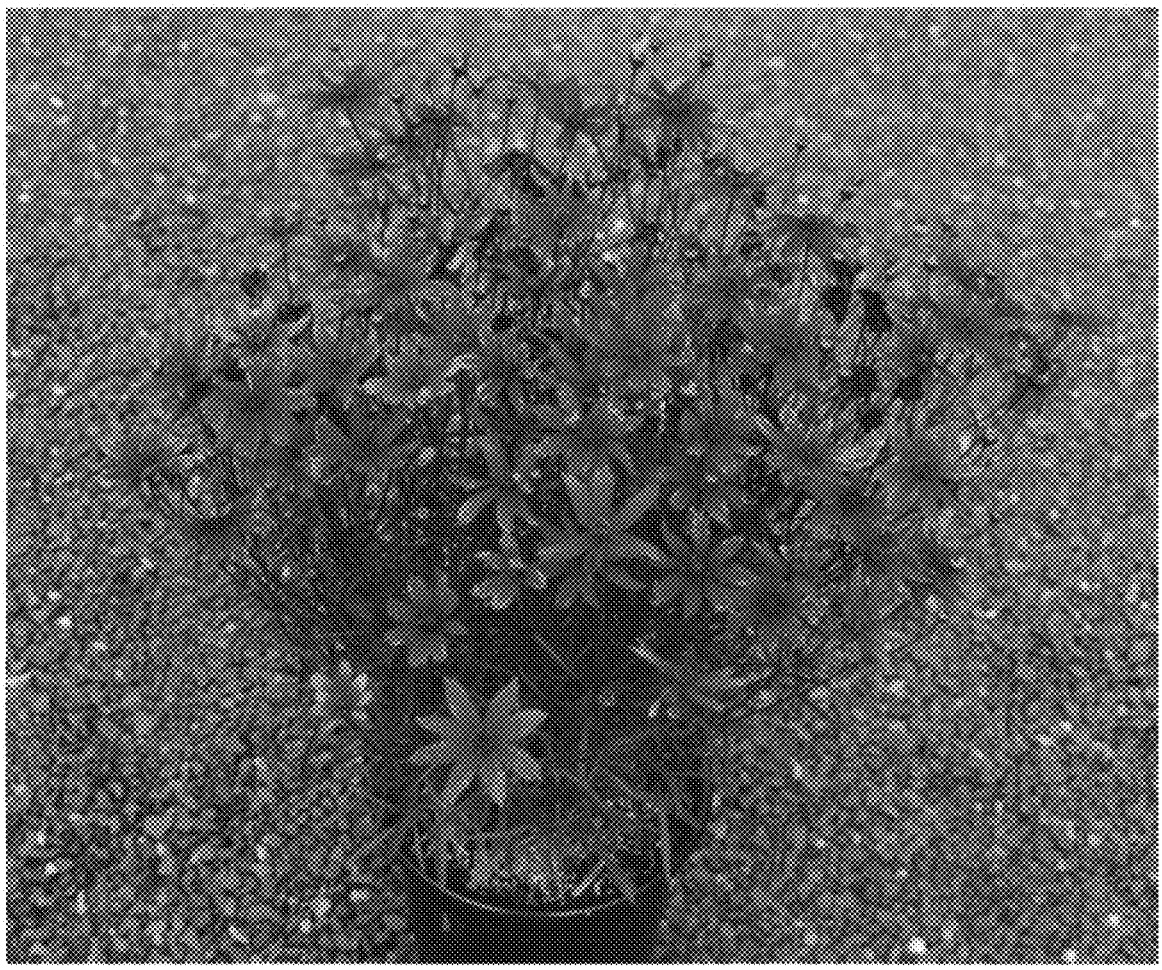
Figure 2:
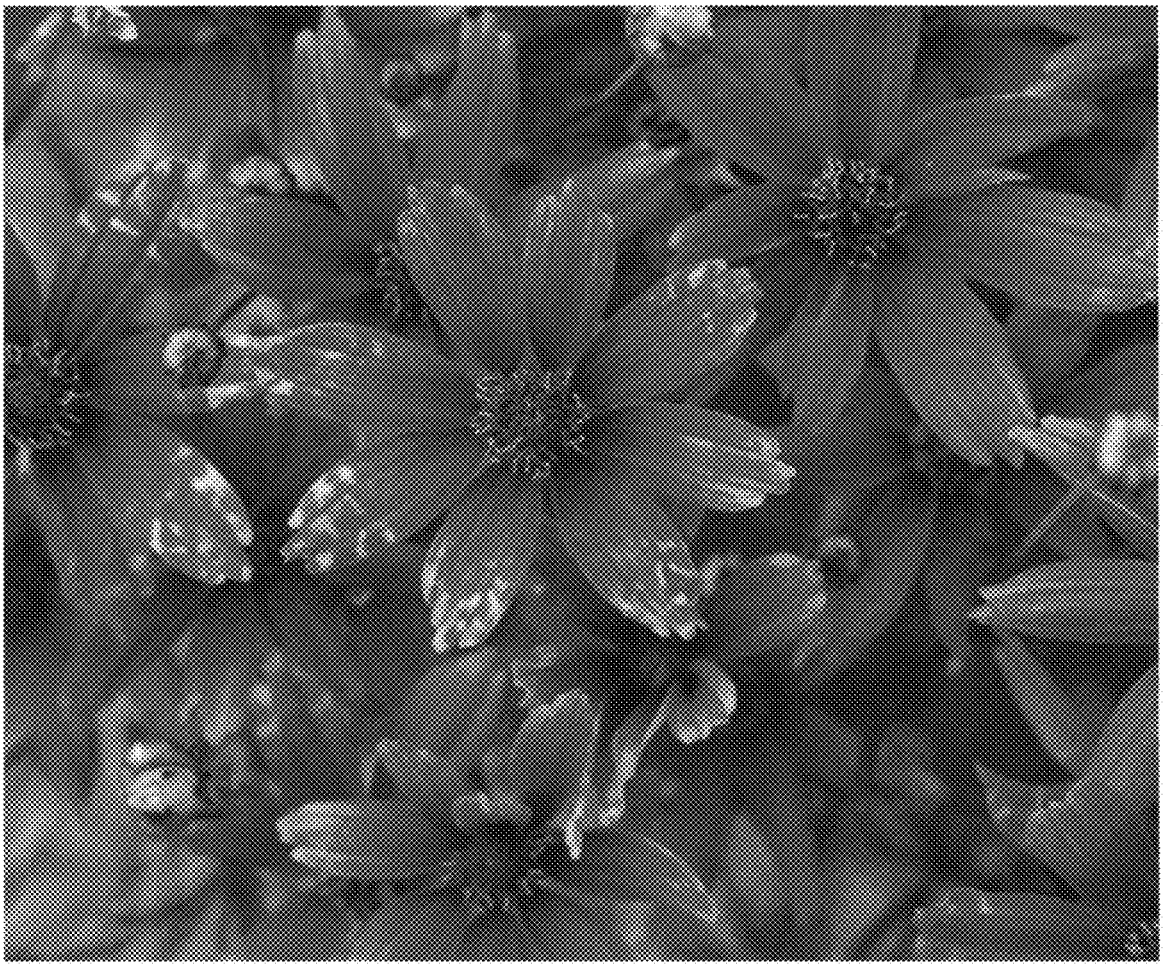

The photograph in FIG. 2 provides a close-up view of the inflorescences of 'Glowing Embers'.

The colors in the photographs are as close as possible with the photographic and printing technology utilized and the color values cited in the detailed botanical description accurately describe the colors of the new *Coreopsis*.

DETAILED BOTANICAL DESCRIPTION

The following is a detailed description of 3-month-old plants of 'Glowing Embers' as grown outdoors in a one-gallon container in Kensington, Conn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Blooms from early July until frost in Kensington, Conn.

*Plant type.*—Herbaceous perennial.

*Plant habit.*—Clump-forming, compact, upright leafy flowering stems with inflorescences held above the foliage.

*Height and spread.*—An average of 34 cm in height and 37 cm in width as grown in a one-gallon container and an average of 45 cm in height and 75 cm in width as grwon in the landscape.

*Cold hardiness.*—At least to U.S.D.A Zone 5a.

*Diseases and pests.*—Resistance to powdery mildew (*Podosphaera macularis*) and leafspot (*Pseudomonas cichorii*), no susceptibility or resistance to pests has been observed.

*Root description.*—Fibrous and fine, NN155A in color.

Growth and propagation:

*Propagation.*—Stem cuttings.

*Time required for root initiation.*—An average of 10 days for root initiation.

*Growth rate.*—Vigorous.

Stem description:

*Shape.*—Rounded to tetragonal, solid.

*Stem color.*—146A.

*Stem strength.*—Strong.

*Stem size.*—Main stems; an average of 15 cm in length and 4 mm in width, lateral stems; an average of 15 cm in length (excluding peduncles) and 2 mm in width.

*Stem surface.*—Glabrous, smooth, and dull.

*Branching habit.*—Freely branched, an average of 17 basal main stems, lateral stems typically branched as oppositely arranaged pairs at each node, with an average of 4 lateral stems (2 pairs) per main stem.

*Internode length.*—An average of 2 cm.

Foliage description:

*Leaf division.*—Simple.

*Leaf margins.*—Entire.

*Leaf size.*—Entire leaves; an average of 8 cm in length and 9 cm in width, ranges from 3 to 4 to 5 leaves; center lobe an average of 5 cm in length and 4 mm in width, lateral lobes an average of 4 cm in length and in 3 mm width.

*Leaf shape.*—Narrow obanceolate.

*Leaf base.*—Cuneate.

*Leaf apex.*—Acute.

*Leaf venation.*—Pinnate, inconspicuous, same color as leaf.

*Leaf attachment.*—Sessile.

*Leaf arrangement.*—Opposite.

*Leaf surface.*—Upper and lower surfaces; smooth, dull, and glaucous.

*Leaf color.*—Young and mature upper and lower surface; 146A.

Flower description:

*Inflorescence type.*—Composite with a single row of ray florets surrounding disk florets in the center, forming a radiant head, inflorescences are borne on branch terminals in loose corymbs.

*Lastingness of inflorescence.*—8 to 10 days until senescence of ray flowers, Phyllaries and disk flowers are persistent.

*Fragrance.*—None.

*Quantity of inflorescences.*—Free flowering, an average of 5 corymbs per main branch, an average of 3 composites per corymb.

*Inflorescence size.*—Corymbs; an average of 9 cm in length and 4 cm in width, composite; an average of 1 cm in depth and 5 cm in diameter with disk portion up to 8 mm in diameter.

*Inflorescence buds.*—Globose in shape, an average of 7 mm in depth and diameter, smooth and shiny surface; color; 163A, suffused at the base with 146A, streaks of 183A held at the margins.

*Peduncle.*—Rounded in shape, strong, an average of 8 cm in length and 1 mm in diameter, 146A in color, smooth and glabrous surface.

Phyllaries (involucral bracts):

*Phyllary number.*—2 rows; outer (lower) row 8, inner (upper) row 8.

*Phyllary arrangement.*—Outer (lower) phyllaries; 50% fused, held upwards with the apex and mid-section recurved downwards, inner (upper) phyllaries; overlap and surround receptacle with apical portion slightly reflexed (campanulate-like).

*Phyllary size.*—Outer (lower) phyllaries; an average of 3 mm in length and 2 mm in width, inner (upper) phyllaries; an average of 6 mm in length and 4 mm in width.

*Phyllary color.*—Upper and lower surfaces, outer (lower) phyllaries; 144A, margins 142B, inner (upper) phyllaries; transluscent, 163A, margins and tip flushed with 178A.

*Phyllary texture.*—Outer (lower) phyllaries; glabrous and smooth on both surfaces, inner (upper) phyllaries; glabrous and slightly waxy on both surfaces.

*Phyllary apex.*—Acute.

*Phyllary base.*—Truncate.

*Phyllary shape.*—Outer (lower) phyllaries; elliptic to lanceolate, inner (upper) phyllaries; lanceolate.

Ray florets (sterile):

*Number.*—8.

*Shape.*—Oblanceolate, with the appearance of 3 longitudinal sections.

*Size.*—An average of 2.5 cm in length and 1 cm in width.

*Apex.*—Rounded with three rounded lobes.

*Base.*—Cuneate.

*Margins.*—Entire on sides with lobed and notched apex.

*Aspect.*—Held mainly horizontal and slightly upwards, perpendicular to peduncle.

*Texture.*—Both surfaces; glabrous, dull, and satiny.

*Color.*—Upper surface when opening; base to center; N34A, center to tip 5A, lower surface when opening; 5A, upper surface when half open; N34A with streaks and specks of 5A on the upper one third toward the apex, upper surface when half open; 11A, upper surface when fully open; N45A with very base suffused with 187A and streaks and specks of toward apex with specks decreasing to absent as it matures further, lower surface when fully open; 11A, slightly streaked with 187A.

Disk florets (male and female):

*Number.*—An average of 70.

*Shape.*—Tubular, corolla is fused, flared at apex.

*Size.*—About 5 mm in length and 0.5 mm in width.

*Color.*—En masse; 21A, corolla; (tube) transluscent, 160B, flared portion 166B.

*Receptacle.*—An average of 6 mm in diameter and 1 mm in depth, 146A in color.

Reproductive organs:

*Presence.*—Disk flowers only.

*Gynoecium.*—1 Pistil; an average of 7 mm in length, style; very fine and 160B in color, bifid pillose, stigma; 163B in color with recurved branches about 0.5 mm in length, ovary is inferior, oblong in shape, an average of 1 mm in length and 0.5 mm in width, and 144C in color.

*Androecium.*—4 stamens, fused into tube surrounding style, an average of 3 mm in length and less than 0.5 mm in width, 202A in color, pollen is minimal in quantity and 163B in color.

*Seed.*—Seed development has been observed to be very minimal; nearly sterile, plants available for data collection did not set seed.

It is claimed:

1. A new and distinct cultivar of *Coreopsis* plant named 'Glowing Embers' as herein illustrated and described.

* * * * *